United States Patent [19]

Hiraga et al.

[11] 4,334,915
[45] Jun. 15, 1982

[54] PHENOXYPHTHALATES AND HERBICIDE CONTAINING THE SAME

[75] Inventors: Kunikazu Hiraga, Izumi; Masakazu Shibayama, Takatsuki; Katsumasa Ohkawa; Tatsuo Harada, both of Kawachinagano, all of Japan

[73] Assignee: Nihon Nohyaku Co. Ltd., Tokyo, Japan

[21] Appl. No.: 123,820

[22] Filed: Feb. 22, 1980

[30] Foreign Application Priority Data

Sep. 2, 1978 [JP] Japan .................. 53-107843

[51] Int. Cl.³ ............... A01N 37/40; C07C 69/80
[52] U.S. Cl. ........................................ 71/108; 560/65
[58] Field of Search ............... 71/108, 112; 560/65

[56] References Cited

U.S. PATENT DOCUMENTS

| | | | |
|---|---|---|---|
| 3,957,852 | 5/1976 | Fujikawa et al. | 560/65 |
| 4,104,280 | 8/1978 | Ackrell | 549/12 |
| 4,124,370 | 11/1978 | Yu | 71/78 |
| 4,128,574 | 12/1978 | Markezich | 562/473 |

FOREIGN PATENT DOCUMENTS 1543964 11/1979 United Kingdom .

OTHER PUBLICATIONS

Heath et al., Chem. Abst., vol. 77 (1972), 114086c.
Rozc et al., Chem. Abst., vol. 84 (1976), 30115t.

*Primary Examiner*—Catherine L. Mills
*Attorney, Agent, or Firm*—Cushman, Darby & Cushman

[57] ABSTRACT

A phenoxyphthalate of the formula

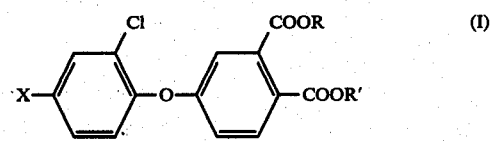

wherein X represents chlorine atom or trifluoromethyl group and R and R' represent methyl or ethyl group, is novel and has a strong herbicidal activity.

19 Claims, No Drawings

PHENOXYPHTHALATES AND HERBICIDE CONTAINING THE SAME

This invention relates to phenoxyphthalates represented by the following formula (I):

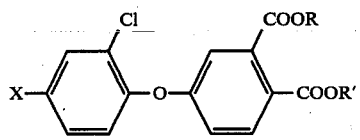

wherein X represents chlorine atom or trifluoromethyl group and R and R' represent methyl or ethyl group, as well as to herbicides containing them as active ingredient.

The phenoxyphthalates represented by the above-mentioned formula (I) are novel compounds and have a strong herbicidal activity, and they are useful as an active ingredient of herbicide.

The compounds of general formula (I) wherein X is chlorine atom can be synthesized, for example, according to a process schematically shown below:

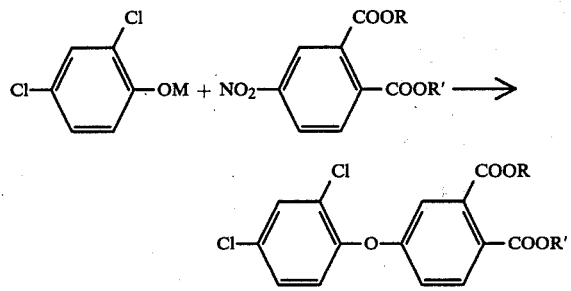

wherein M represents alkali metal atom, and R and R' are same as defined above.

That is, they can easily be synthesized by allowing an alkali metal salt of 2,4-dichlorophenol to react with 4-nitrophthalate ester in an appropriate solvent, for example aprotic polar solvents such as dimethylformamide, dimethylacetamide, dimethyl sulfoxide or the like. Generally, the reaction can be conducted at a temperature ranging from room temperature to the boiling point of the solvent.

On the other hand, the compounds of general formula (I) wherein X is trifluoromethyl group can be synthesized, for example, according to a process schematically shown below:

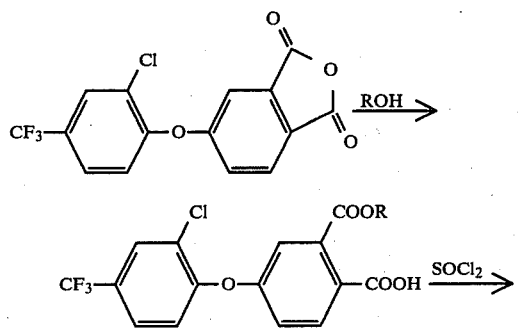

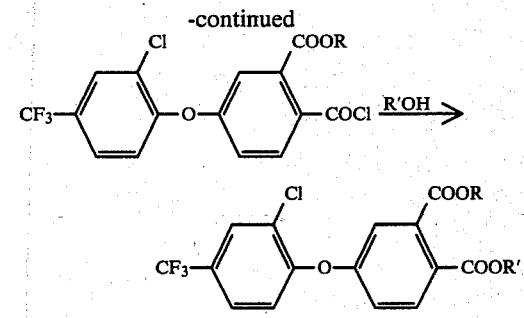

wherein R and R' are same as defined above.

That is, they can be synthesized by allowing a phthalic acid monoester, obtainable by refluxing 4-(2'-chloro-4'-trifluoromethylphenoxy)-phthalic anhydride with an excessive quantity of the alcohol to react with an appropriate chlorinating agent such as thionyl chloride, phosphorus pentachloride or the like, followed by refluxing the chlorinated product together with an excessive quantity of the alcohol (R'OH) in the presence or absence of an appropriate base such as pyridine, triethylamine or the like. In the above-mentioned scheme, the intermediate products are generally obtained in the form of mixture. Therefore, when reactant ROH differs from reactant R'OH, the final product is obtained as a mixture comprising approximately equal quantities of mixed esters which are generally difficult to separate.

Herein, said 4-(2'-chloro-4'-trifluoromethylphenoxy)-phthalic anhydride (m.p. 72°–74° C.) can be synthesized, for example, according to the route schematically shown below:

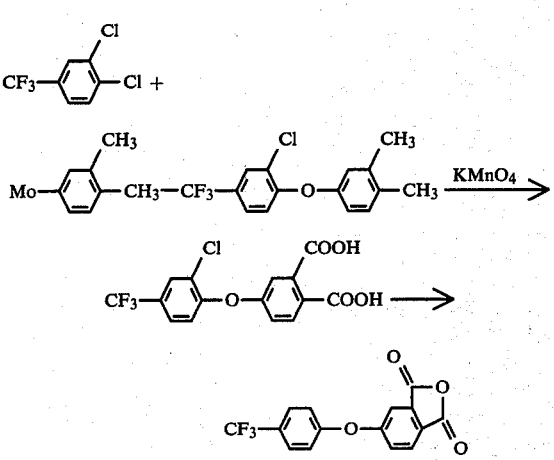

b.p. 120–125° C./0.1 mmHg
m.p. 162–164° C.

Typical examples of the compounds represented by the formula (I) are shown in Table 1.

TABLE 1

| No. | X | R | R' | | $n_D^{30}$ (refractive index) |
|---|---|---|---|---|---|
| 1 | Cl | CH$_3$ | CH$_3$ | | 1.5853 |
| 2 | CF$_3$ | CH$_3$ | CH$_3$ | | 1.5318 |
| 3 | CF$_3$ | C$_2$H$_5$ | C$_2$H$_5$ | | 1.5202 |
| 4 | Cl | C$_2$H$_5$ | C$_2$H$_5$ | | 1.5570 |
| 5 | CF$_3$ | CH$_3$ | C$_2$H$_5$ | mixture (ca. 1:1) | 1.5250 |

TABLE 1-continued

| No. | X | R | R' | $n_D^{30}$ (refractive index) |
|---|---|---|---|---|
| | CF$_3$ | C$_2$H$_5$ | CH$_3$ | |

The compounds represented by the above-mentioned formula (I) have a strong herbicidal activity to typical strongly injurious weeds including those known as strongly injurious weeds grown in paddy field such as barnyard grass (*Echinochloa Crusgalli* L., annual gramineous weed), umbrella plant (*Cyperus difformis* L., annual cyperaceous weed), Hotarui (*Scirpus juncoides* Roxb. var hotarui ohwi., perennial cyperaceous weed), arrowhead (*Sagittaria pygmaes* Miq., perennial weed of Alismataceae family) and the like and those known as strongly injurious weeds grown in upland field such as barnyard grass (aforesaid), large crabgrass (*Digitaria adscendeus* Henr. annual gramineous weed), green amaranth (*Amaranthus viridis* L., annual weed of Amaranthaceae family), mugwort (*Artemisia princeps* Pamp., perennial weed of Asteraceae family) and the like and to other various injurious weeds. However, at the same time, the compounds represented by the formula (I) can control the above-mentioned injurious weeds with such a low dosage as to exercise no chemical injury on, for example, rice plant, so that they are useful also as selective herbicide. In addition, since their herbicidal activity can effectively be exhibited by both pre-emergence and post-emergence applications, the compounds of general formula (I) are useful as a pre-emergence treating agent and as a post-emergence treating agent for weeds. In case where they are used as a selective post-emergence treating agent, it is effective to apply the agent from the period at which the weeds are yet in the infant stage of growth.

Particularly preferable compounds include the followings:

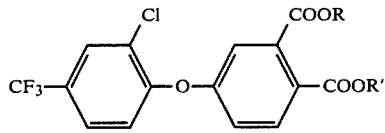

wherein R and R' are same as defined above and most preferable is dimethyl 4-(2'-chloro-4'-trifluoromethylphenoxy)phthalate.

The compounds represented by the formula (I) are formed into preparations having appropriate form according to the conventional procedure in the pesticidal preparation making and then put to use for the purpose of weed control.

That is, the above-mentioned compounds are incorporated with an appropriate inert carrier in an appropriate proportion together with auxiliary agents, if necessary, and dissolved into, dispersed into, suspended in, mixed with, impregnated into, adsorbed on or attached to the carrier, after which they are made into an appropriate preparation form such as suspension, emulsifiable concentrate, wettable powder, dust, granule, tablet or the like.

The inert carrier used in this invention may be any of solid and liquid. Examples of the material usable as the solid carrier include vegetable powders such as soybean flour, cereal flour, wood flour, bark flour, saw dust, powdered tabacco stalk, powdered walnut shell, bran, powdered cellulose and extraction residues of vegetables; fibrous materials such as paper, corrugated fiberboards and rags; synthetic polymers such as powdered synthetic resins; inorganic mineral powders such as clays (for example, kaolinite, clay, bentonite, and acid clay), talcs (for example, talc and pyrophyllite), siliceous substances [for example, diatomaceous earth, siliceous sand, mica and white carbon (highly dispersible synthetic silicic acid, also called finely divided hydrated silicon or hydrated silicic acid; some products contain calcium silicate as the major ingredient)], active charcoal, pumice, calcined diatomaceous earth, disintegrated brick, fly ash, sand, calcium carbonate, calcium phosphate and the like; chemical fertilizers such as ammonium sulfate, ammonium phosphate, ammonium nitrate, urea, ammonium chloride and the like; and farmyard manure. They may be used either alone or in the form of mixture of two or more. The material usable as said liquid carrier is selected from those which can act as solvent for the active compound in themselves as well as those which cannot act as solvent for the active compound but can disperse the active compound by the aid or an auxiliary agent. Examples of said material include the followings, which may be used either alone or in the form of mixture of two or more: water; alcohols such as methanol, ethanol, isopropanol, butanol, and ethylene glycol; ketones such as acetone, methyl ethyl ketone, methyl isobutyl ketone, diisobutyl ketone and cyclohexanone; ethers such as ethyl ether, dioxane, cellosolves, dipropyl ether and tetrahydrofuran; aliphatic hydrocarbons such as gasoline and mineral oil; aromatic hydrocarbons such as benzene, toluene, xylene, solvent naphtha and alkylnaphthalene; halogenated hydrocarbons such as dichlorethane, chlorobenzenes, chloroform and carbon tetrachloride; esters such as ethyl acetate, dibutyl phthalate, diisopropyl phthalate and dioctyl phthalate; acid amides such as dimethylformamide, diethylformamide and dimethylacetamide; nitriles such as acetonitrile; dimethyl sulfoxide; and the like.

As said auxiliary agents, the followings can be referred to. These auxiliary agents are used in accordance with the object. In some cases, two or more kinds of auxiliary agents are used in combination. In some other cases, no auxiliary agent may be used at all. A surfactant is used for the purpose of emulsifying, dispersing, solubilizing and/or wetting active compound. Examples of said surfactant include the followings: polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonic acid salts, naphthalenesulfonic acid condensates, ligninsulfonic acid salts, higher alcohol sulfuric esters and the like. For the purpose of stabilization of dispersions, tackification or agglomeration of the active compound, it is possible to use, for example, casein, gelatin, starch, alginic acid, methylcellulose, carboxymethylcellulose, gum arabic, polyvinyl alcohol, turpentine oil, rice bran oil, bentonite, ligninsulfonic acid salts and the like.

For the purpose of improving the flow properties of solid products, it is possible to use waxes, stearic acid salts, alkyl esters of phosphoric acid and the like.

As peptizer for dispersible compositions, it is possible to use naphthalenesulfonic acid condensates, polyphosphoric acid salts and the like.

It is also possible to add a defoaming agent such as silicone oils and the like.

The proportion of the active compound in the composition can be varied as required. In the case of dust or granule, the suitable proportion of active compound is usually in the range of 0.5-20% by weight. In the case of emulsifiable concentrate or wettable powder, it is 0.1-50% by weight.

For decaying various weeds or inhibiting their growth or protecting useful plants from the injury due to weeds, a cuantity necessary for effectively killing weeds or inhibiting their growth of the herbicide of this invention is applied, in the form of an appropriate dilution with water or suspension in water, to said weeds or to the place where the emergence or growth of said weeds is undesirable, by the method of foliage treatment, soil treatment or water treatment.

The amount used of the herbicide of this invention varies depending on various factors, such as weed to be controlled, state of emergence or growth of weed, tendency of the emergence of weed, weather, environmental conditions, preparation form, method of application, place of application, time of application, etc.

The herbicide of this invention is generally applied in a proportion of 50-1,000 g or more active compound per 10 ares.

When the herbicide of this invention is used as a selective herbicide, it is recommendable to select the dosage from the lower range in the above-mentioned dosage range. For example, it is also possible to use the herbicide of this invention in a proportion of 50-250 g/10 ares. Particularly, herbicidal compositions containing compound No. 2 of this invention are useful in that they exhibit an excellent herbicidal effect at a low dosage without any chemical injury.

Examples of this invention will be shown below. This invention is not limited by them.

EXAMPLE 1

Dimethyl 4-(2',4'-dichlorophenoxy)-phthalate (Compound 1)

2.4 g (0.012 mole) of sodium salt of 2,4-dichlorophenol and 2.4 g (0.010 mole) of dimethyl 4-nitrophthalate are dissolved in dry dimethylformamide and stirred at 130°-150° C. for 5 hours. After cooling, the mixture is poured into cold water, extracted with benzene, successively washed with dilute aqueous caustic soda, dilute hydrochloric acid and water, dried over sodium sulfate and then concentrated to obtain 2.5 g of an oily product. It was purified by column chromatography and there was obtained 1.6 g of the intended compound as a viscous oily product. Yield 45%.

EXAMPLE 2

Dimethyl 4-(2'-Chloro-4'-trifluoromethylphenoxy)-phthalate (Compound 2)

2.0 g (0.006 mole) of 4-(2'-chloro-4'-trifluoromethylphenoxy)-phthalic anhydride is dissolved into 100 ml of methanol and heated under reflux for 5 hours, after which the methanol is distilled off to obtain a monomethyl ester derivative. Without isolation thereof, it is heated for one hour under reflux in 20 ml of thionyl chloride (SOCl$_2$) to obtain an acid chloride derivative. After the excessive thionyl chloride is removed, the acid chloride, not isolated, is heated under reflux in 100 ml of methanol for 3 hours. After cooling, the methanol is distilled off, the residue is extracted with benzene, and the benzene layer is washed successively with dilute aqueous caustic soda and water, dried over sodium sulfate and concentrated. Thus, 1.4 g (yield 62%) of the intended product is obtained as an oily product.

Similarly, the above-mentioned reaction product containing acid chloride derivative is reacted with ethanol to obtain a liquid product (n$_D^{30}$ 1.5250) which comprises approximately equal quantities of the following compounds of the formulae:

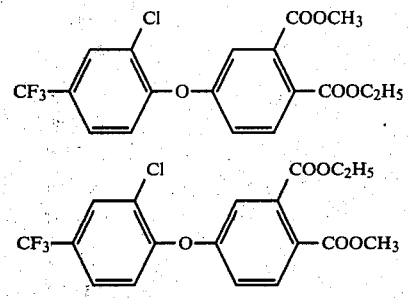

In the examples mentioned below, "parts" are by weight.

EXAMPLE 3

A wettable powder is prepared by uniformly mixing the followings:
Compound 1—20 parts
Diatomaceous earth—75 parts
Nonylphenol polyoxyethylene glycol ether—5 parts

EXAMPLE 4

An emulsifiable concentrate is prepared by dissolving the followings uniformly:
Compound 2—20 parts
Xylene—40 parts
Tetrahydrofuran—25 parts
Calcium dodecylbenzenesulfonate and polyoxyethylene nonylphenol ether—15 parts

EXAMPLE 5

A granular preparation is prepared by mixing together and pulverizing the followings:
Compound 3—5 parts
Clay—50 parts
Bentonite—35 parts
White carbon—5 parts
followed by adding, thereto, the followings:
50% Lignin—10 parts
Water—10 parts
and then uniformly mixing them, forming the mixture into granule by means of an extruding granulator, drying the granules and sieving them.

In order to prove the effectiveness of the herbicide of this invention, some test examples are shown below.
Test Example 1
(Effect against paddy field weeds of various leaf stages and chemical injury)

A number of 1/10,000 are pots were filled with soil to simulate the state of paddy field, in which injurious weeds of the following leaf stages were grown. The day before the treatment with test agent, seedlings of paddy field rice at the 2.5-leaved stage were transplanted thereinto. The pots were treated by means of spray with an aqueous dilution of emulsifiable concentrate so that the amount of active ingredient applied just came to the appointed dosage. 21 days after the treatment, the herbicidal effect and the extent of chemical injury to rice plant were investigated. The results are shown in Table 2.

Leaf stages of injurious weeds:
  Barnyard grass—1-leaved stage
  Monochoria—2-3-leaved stage
  Umbrella plant—ditto
  Hotarui—ditto
  Arrowhead—3-leaved stage Evaluation:
  5: Weeding rate 100%
  4: Weeding rate 90% or more
  3: Weeding rate 80% or more
  2: Weeding rate 60% or more
  1: Weeding rate less than 60% (including 0%)

TABLE 2

| Test compound | Amount of active ingredient (g/are) | Barnyard grass | Monochoria | Umbrella plant | Hotarui | Arrowhead | Chemical injury |
|---|---|---|---|---|---|---|---|
| 1 | 25 | 4 | 3 | 4 | 3 | 3 | None |
|   | 12.5 | 3 | 3 | 2 | 1 | 3 | None |
| 2 | 25 | 5 | 5 | 5 | 4 | 3 | Slight injury |
|   | 12.5 | 5 | 5 | 5 | 3 | 3 | None |
| 3 | 25 | 4 | 3 | 3 | 2 | 2 | None |
|   | 12.5 | 3 | 2 | 2 | 2 | 2 | None |
| 4 | 25 | 3 | 3 | 3 | 2 | 2 | None |
|   | 12.5 | 3 | 2 | 2 | 1 | 2 | None |
| 5 | 25 | 5 | 5 | 4 | 3 | 2 | None |
|   | 12.5 | 3 | 4 | 3 | 2 | 2 | None |
| A | 20 | 5 | 4 | 4 | 3 | 1 | Considerable injury |
| B | 50 | 1 | 3 | 3 | 1 | 1 | None |
| C | 50 | 1 | 1 | 1 | 1 | 1 | None |
| D | 50 | 1 | 1 | 1 | 1 | 1 | None |
| E | 50 | 1 | 1 | 1 | 1 | 1 | None |
| F | 50 | 1 | 1 | 1 | 1 | 1 | None |

(Note)
A: Commercial emulsifiable concentrate of NIP, containing 2,4-dichloro-4'-nitrodiphenyl ether as active ingredient
B: Dimethyl 4-(4'-methylphenoxy)-phthalate
C: Diethyl 4-(4'-methylphenoxy)-phthalate
D: Diisopropyl 4-(4'-methylphenoxy)-phthalate
E: Dimethyl 4-(4'-chlorophenoxy)-phthalate
F: Diethyl 4-(4'-chlorophenoxy)-phthalate Test Example 2
(Effect against paddy field weeds in the early stage of emergence)

A number of 1/10,000 are pots were filled with soil to simulate the state of paddy field, in which the weeds shown in the following table were grown so that they are all in the early stage of emergence simultaneously. The treatment with test agent was carried out in the same manner as in Text Example 1, and the effect was evaluated. The results are shown in Table 3.

TABLE 3

| Test compound | Amount of active ingredient (g/are) | Barnyard grass | Monochoria | Umbrella plant | Hotarui | Arrowhead |
|---|---|---|---|---|---|---|
| 1 | 25 | 5 | 5 | 5 | 3 | 4 |
|   | 12.5 | 5 | 5 | 5 | 2 | 2 |
|   | 6.25 | 5 | 5 | 5 | 1 | 1 |
| 2 | 25 | 5 | 5 | 5 | 5 | 5 |
|   | 12.5 | 5 | 5 | 5 | 5 | 5 |
|   | 6.25 | 5 | 5 | 5 | 5 | 4 |
| 3 | 25 | 5 | 5 | 5 | 4 | 5 |
|   | 12.5 | 5 | 5 | 5 | 3 | 4 |
|   | 6.25 | 5 | 5 | 5 | 2 | 2 |
| 4 | 25 | 5 | 5 | 5 | 2 | 3 |
|   | 12.5 | 5 | 4 | 5 | 1 | 1 |
|   | 6.25 | 4 | 4 | 3 | 1 | 1 |
| 5 | 25 | 5 | 5 | 5 | 5 | 5 |
|   | 12.5 | 5 | 5 | 5 | 3 | 4 |
|   | 6.25 | 5 | 5 | 5 | 3 | 2 |
| B | 50 | 2 | 2 | 3 | 1 | 1 |
| C | 50 | 1 | 2 | 1 | 1 | 1 |
| D | 50 | 1 | 1 | 1 | 1 | 1 |
| E | 50 | 2 | 2 | 4 | 3 | 3 |
| F | 50 | 1 | 2 | 2 | 1 | 1 |

(Note) B, C, D, E, F: The same as above.

Test Example 3
(Effect of pre-emergence treatment on upland field weeds and the chemical injury)

Polyethylene vats (10 cm × 20 cm × 5 cm depth) were filled with soil, which was seeded in drills with rice and the weeds shown in the following table. The seeds were covered with 1 cm of soil and the treatment with test agent and the evaluation of effect were carried out in the same manner as in Test Example 1. The results are shown in Table 4.

TABLE 4

| Test compound | Amount of active ingredient (g/are) | Herbicidal effect | | | | Chemical injury |
|---|---|---|---|---|---|---|
| | | Barnyard grass | Large crabgrass | Green amaranth | Mugwort | |
| 1 | 25 | 2 | 3 | 5 | 4 | None |
|   | 12.5 | 1 | 1 | 4 | 3 | None |
| 2 | 25 | 3 | 5 | 5 | 5 | None |
|   | 12.5 | 3 | 5 | 5 | 5 | None |
| 3 | 25 | 3 | 5 | 5 | 5 | None |
|   | 12.5 | 1 | 4 | 5 | 4 | None |
| 4 | 25 | 1 | 2 | 5 | 4 | None |
|   | 12.5 | 1 | 1 | 2 | 2 | None |
| 5 | 25 | 3 | 5 | 5 | 5 | None |
|   | 12.5 | 2 | 5 | 5 | 4 | None |
| A | 25 | 5 | 5 | 4 | 3 | Strong injury |
|   | 12.5 | 3 | 5 | 3 | 2 | Strong injury |
| B | 50 | 1 | 1 | 2 | 2 | None |
| C | 50 | 1 | 1 | 2 | 2 | None |
| D | 50 | 1 | 1 | 2 | 2 | None |
| E | 50 | 1 | 1 | 1 | 2 | None |
| F | 50 | 1 | 1 | 1 | 1 | None |

(Note) A, B, C, D, E, F: The same as above.

What is claimed is:

1. A phenoxyphthalate compound represented by the formula (I):

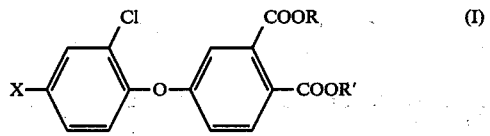

wherein X represents chlorine atom or trifluoromethyl group, and R and R' represent methyl or ethyl group.

2. The phenoxyphthalate compound of claim 1, wherein R and R' are both ethyl group.

3. The phenoxyphthalate compound of claim 1, wherein R and R' are both methyl group.

4. The phenoxyphthalate compound of claim 1, which consists of a mixture of a compound wherein R is ethyl group and R' is methyl group with a compound wherein R is methyl group and R' is ethyl group.

5. The phenoxyphthalate compound of claim 1, wherein X is trifluoromethyl group.

6. Dimethyl 4-(2'-chloro-4'-trifluoromethylphenoxy)phthalate.

7. A herbicidal composition comprising an effective amount of a phenoxyphthalate compound represented by the formula

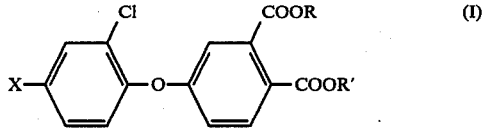

wherein X represents chlorine atom or trifluoromethyl group, and R and R' represent methyl or ethyl group, and a carrier.

8. A process of killing plants comprising applying to the plants a herbicidally effective amount of a phenoxyphthalate of claim 1.

9. The process according to claim 8 wherein R and $R^1$ are both ethyl.

10. The process according to claim 8 wherein R and $R^1$ are both methyl.

11. The process according to claim 8 wherein there is employed a mixture of two phenoxyphthalates wherein in one compound R is ethyl and $R^1$ is methyl and in the other compound R is methyl and $R^1$ is ethyl.

12. The process of claim 8 wherein X is trifluoromethyl.

13. The process of claim 12 wherein R and $R^1$ are both methyl.

14. The process of claim 8 wherein the herbicide is applied to a rice field and is used in an amount effective to kill the weeds in the field but insufficient to damage the rice.

15. The process of claim 14 wherein X is trifluoromethyl.

16. The process of claim 15 wherein R and $R^1$ are both methyl.

17. The process of claim 14 wherein the weeds comprise barnyard grass, monochoria, umbrella plant, Hotarin, arrowhead, crabgrass, mugwort and green amaranth.

18. The process of claim 17 wherein X is trifluoromethyl and R and $R^1$ are both methyl.

19. The process of claim 18 wherein the herbicide is used in an amount of 50–250 g/10 ares.

* * * * *